March 11, 1958 M. L. V. VAN ZANTEN Plant Pat. 1,686
AZALEA PLANT
Filed May 13, 1957 2 Sheets-Sheet 1
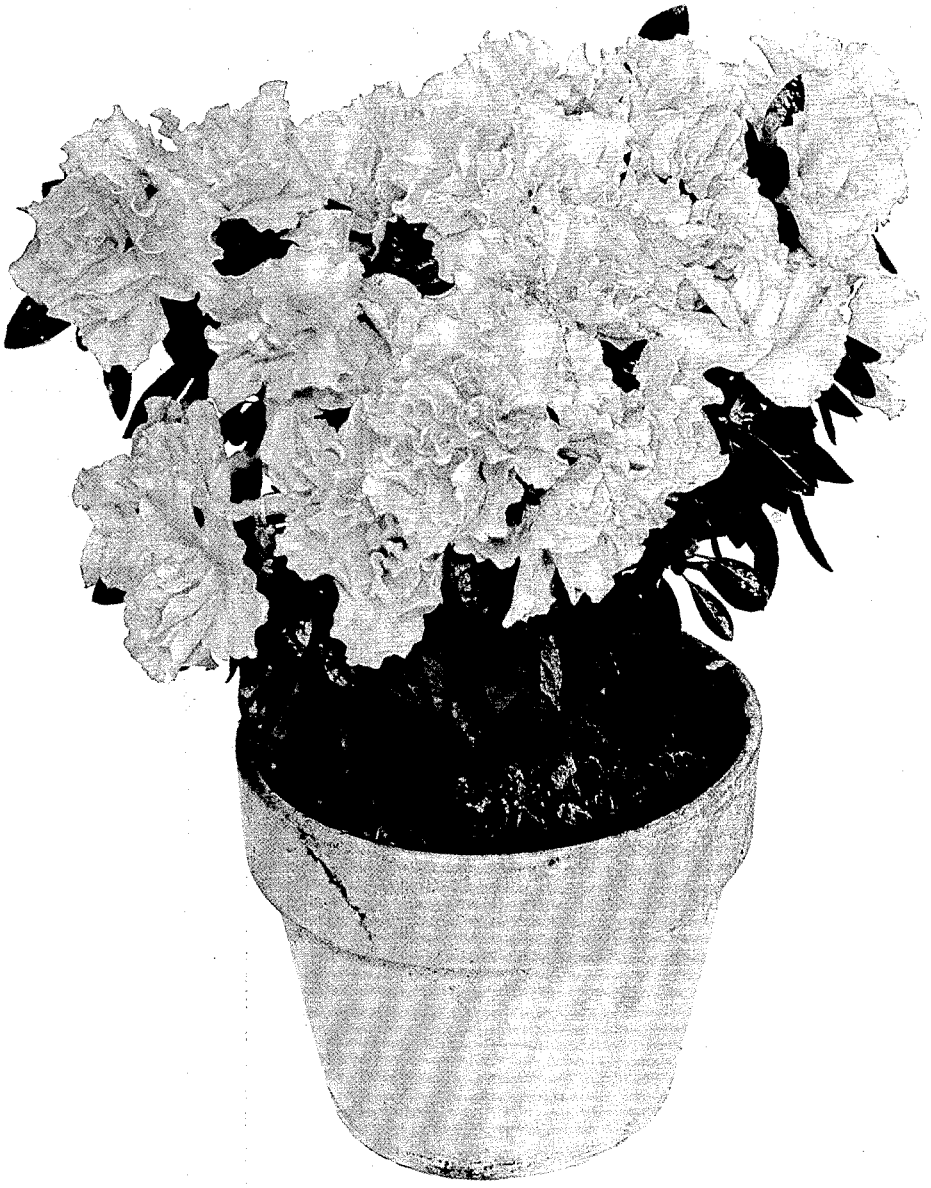
INVENTOR
MAURITS L. V. VAN ZANTEN
BY F. R. Geisler.
ATTORNEY March 11, 1958 M. L. V. VAN ZANTEN Plant Pat. 1,686
AZALEA PLANT
Filed May 13, 1957 2 Sheets-Sheet 2
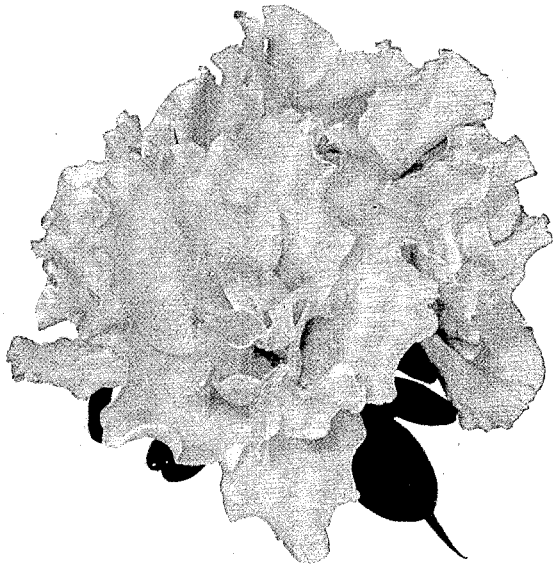
INVENTOR
MAURITS L. V. VAN ZANTEN
BY F. A. Gerstler.
ATTORNEY United States Patent Office Plant Pat. 1,686
Patented Mar. 11, 1958

1,686

AZALEA PLANT

Maurits L. V. Van Zanten, Lynden, Wash.

Application May 13, 1957, Serial No. 658,903

1 Claim. (Cl. 47—60)

This invention comprises a new and distinct variety of azalea, the novel characteristics of which are particularly its habit of easy rooting and of forming a good root system, its strong and rapid growth and its large and double flowers of cherry crimson color.

The present azalea resulted from a cross between two double Indica azaleas, namely the Memoire de Charles Vuylstake (used as the female plant) and the Prosper Van den Dael, both of which are unpatented. The purpose of the crossing was to obtain a new and improved azalea with double red flowers which would possess good growing qualities, especially with regard to rooting and subsequent root formation so as to eliminate the necessity of grafting.

The cross pollination was performed by me on March 17, 1945, in my greenhouse in Lynden, Washington, and the usual method was followed of hand-pollenizing stigma with pollen of the male plant. The resulting seed was planted in the spring of 1946 and this particular seedling was segregated and retained because of its rooting characteristics and its root formation and also because of the shape of the plant, the habit of growth which it showed, as well as the texture of the foliage, bud formation, and the substance and color of the flowers.

During the following years, propagation took place under my supervision in Lynden, Washington both by grafting and by cuttings, and both methods appeared to be equally satisfactory and practicable.

The accompanying illustrations actually show one of these plants in bloom and also show a closeup view of the flowers of the same.

The following is a detailed description of the plant and its characteristics:

*Shape of plant.*—The plant has a low, compact form, with very strong branches, well spaced, giving the heavy flower trusses ample room to develop.

*Roots.*—A definite characteristic of this plant is the rapid formation and subsequent growth of a solid, firm root system, which makes the plant particularly suitable for mass production (no grafting required) and for long distance shipping. This feature makes the plant distinctive from most other double flowering red Indica azaleas which usually do not root readily and generally form small root balls with resulting slow growth, necessitating expensive grafting as a method of propagating. This new variety, having a good root system, can be grown in the full sun during the summer months, thus eliminating growing under glass, cloth or lath. This constitutes a quite distinctive and valuable feature.

*Foliage.*—The leaves, with a waxy appearance, are medium large, oval shaped, about 1½ to 2½ inches long and ¾ inch wide at the widest part. The color of the upper side of the leaves is Ivy Green (Horticultural Color Chart 0001060/3, page 200) whereas the underside is Spinach Green (Horticultural Color Chart 0960/2 page 187). The leaves are well distributed on the branches. Foliage and stems are of a very strong texture.

*Flower buds.*—The flower buds are well distributed over the entire plant, partly single and partly in clusters, containing up to five heavy buds. The budset takes place early in the season, in July or early August. The individual trusses are spaced in such a way that there is ample room for the large flowers to develop properly.

*Flowers.*—The color of the flowers is between Cherry (Horticultural Color Chart 722/1) and Crimson (Horticultural Color Chart 22/1, page 22), whereas the blotch in the lower part of the petals is Cardinal Red (Horticultural Color Chart 822, page 168). Pistil and anthers are the same color as the flowers. The individual flowers measure from 3 to 3½ inches across, and are fully double with gently ruffled edges. Petals measure 1½ inches across and 1½ inches high.

*Characteristics of growth and blooming.*—In its class, as a typical double Indica (Belgian) azalea, it has the distinct quality of producing a well developed, salable plant in a short time (one to two years) without the necessity of grafting on an understock. Having a good, solid root ball, it is very suitable for long distance shipping in the Fall. The plant can be forced from December on under normal greenhouse conditions and, if kept cooler, can be used for February or later forcing. The flowers are of good substance and stay on the plant a long time. The plant can be grown in the open, in the full sun, without special protection (during the summer months). Having tendencies of both good root growth and early definite budset, the plant is adaptable for one or two year culture from its own root, producing desirable material for the florist trade, especially where small or medium sized plants for early and later forcing are required.

Having thus disclosed by invention, I claim:

A new and distinct variety of azalea plant substantially as herein described, characterized particularly by its habit of easy rooting and of forming a good root system, its compact form, its early blooming and forcing qualities, its strong and rapid growth, and its large and fully double flowers of Cherry-crimson color.

No references cited.